(12) United States Patent
Johansson et al.

(10) Patent No.: US 7,779,666 B2
(45) Date of Patent: Aug. 24, 2010

(54) METHOD FOR CHECKING THE CONDITION OF A SAMPLE WHEN METERING LIQUID

(75) Inventors: Henrik Johansson, Espoo (FI); Olli Myyryläinen, Helsinki (FI); Juha Nummipuro, Espoo (FI)

(73) Assignee: Thermo Fisher Scientific Oy, Vantaa (FI)

( * ) Notice: Subject to any disclaimer, the term of this patent is extended or adjusted under 35 U.S.C. 154(b) by 534 days.

(21) Appl. No.: 11/665,023

(22) PCT Filed: Oct. 11, 2004

(86) PCT No.: PCT/FI2004/000602

§ 371 (c)(1),
(2), (4) Date: Apr. 10, 2007

(87) PCT Pub. No.: WO2006/040386

PCT Pub. Date: Apr. 20, 2006

(65) Prior Publication Data

US 2009/0007628 A1    Jan. 8, 2009

(51) Int. Cl.
*G01F 19/00* (2006.01)
(52) U.S. Cl. ........................................ 73/1.74
(58) Field of Classification Search .......... 73/1.74, 73/864.11, 864.12, 864.22, 864.01; 222/36–38, 222/55, 57, 63, 64, 66, 148, 333, 1
See application file for complete search history.

(56) References Cited

U.S. PATENT DOCUMENTS

| | | | |
|---|---|---|---|
| 4,780,833 A | 10/1988 | Atake | 700/281 |
| 4,893,515 A | 1/1990 | Uchida | 73/864.34 |
| 6,094,966 A * | 8/2000 | Papen et al. | 73/1.74 |
| 6,121,049 A * | 9/2000 | Dorenkott et al. | 436/50 |
| 6,370,942 B1 | 4/2002 | Dunfee et al. | 73/37 |

FOREIGN PATENT DOCUMENTS

| | | |
|---|---|---|
| EP | 0 571 100 A1 | 11/1993 |
| EP | 0 981 048 A2 | 2/2000 |
| EP | 1 059 535 A1 | 12/2000 |

* cited by examiner

*Primary Examiner*—Hezron Williams
*Assistant Examiner*—Tamiko D Bellamy
(74) *Attorney, Agent, or Firm*—Birch, Stewart, Kolasch & Birch, LLP

(57) ABSTRACT

A method for controlling the dispensation of a liquid volume sample when metering amounts of liquid by sucking into a tube, probe or tip a volume of a liquid to be displaced and ejecting the sample to a different vessel. According to the method the metering act is performed normally and the liquid to be metered is displaced thereafter in a desired vessel. During the metering act and after a desired amount of liquid is sucked into the metering line, a supplementary suction step is performed wherefrom the success of the metering act can be deduced. The pressure function of the supplementary suction step is measured and this function is compared with a calibration function.

20 Claims, 4 Drawing Sheets

METHOD FOR CHECKING THE CONDITION OF A SAMPLE WHEN METERING LIQUID

The present invention relates to a method for controlling the dispensation of a liquid volume sample when metering amounts of liquid by sucking into a tube, probe or tip a volume of a liquid to be displaced and ejecting the sample to a different vessel.

BACKGROUND OF THE INVENTION

Several chemical analysis are done by automatic analyzing equipment, in hospitals and laboratories. For the analysis amounts of liquid sample medium and reagents have to be automatically measured into analyzing vessels. The amounts to be measured are typically very small, in the range of 1-250 µl and the amount to be displaced and transferred must be very accurately controlled. One typical way to meter and transfer liquids is to use a suction tube or needle wherein the amount of sample or reagent is sucked and wherefrom it is ejected to a desired vessel. The pressure differences required for sucking and ejecting the liquid are effected by an accurate metering syringe. The proportioning and transfer of liquids is one of the most vulnerable functions of automatic analyzers and very dependent on the properties of the liquid to be handled. Possible disturbances causing errors in analyzes are deviances in the properties of the sample or reagent like clogging or abnormally high viscosities, failed sucking of the liquid leading to an insufficient or missing metering. Missing suction can be caused by foaming of the sample or by other failures in detection of the surface of the sample.

Detecting the failures in metering is essential to reliable functioning of the apparatus. Since this type of analyzers are often used in medical analysis for diagnosing diseases, no faulty analyzing results can be allowed in any of the samples. Rejection of a correct metering is very undesirable for example since the volumes of the samples are small and not easily replaceable. When the analyzes are used for diagnosing diseases, interpreting a failed metering as a successful one can be even catastrophic.

Presently the metering is controlled by measuring continuously the pressure in the suction line of the metering apparatus. Measurement is done by an accurate and therefore expensive pressure gauge that is connected to the suction line. The gauge can be flow-through type or connected to a branch from the suction line. The control of a successful metering is based on surveillance of the pressure during the metering. The peak values of the pressures during suction and ejection as well as recovery times after process steps are controlled and different algorithms and threshold values are used for determining whether the metering has been successful or not. In some methods surface integration of the pressure functions are used for evaluation by comparing them to calibration values.

Above-mentioned methods are described in patents EP 0981048, U.S. Pat. No. 6,370,942, WO 9208545, EP 0169071, EP 0571100, U.S. Pat. No. 4,780,833 and EP 0289946, for example. A common feature of these apparatuses is the surveillance of the suction or ejection of the liquid and pressure changes related thereto.

The above-mentioned methods are most suitable for detecting clogging of the metering line. These types of methods have anyway several drawbacks. The methods require quite tedious calibration and complex algorithms determining the success of the metering act. This rises the probability of faulty interpretations and maintenance of the system becomes difficult and time-consuming. Since one multifunctional automatic analyzer utilizes normally several metering volumes and different metering cycles and every combination of these has a characteristic pressure curve, it is very tedious to accomplish a valid general calibration and threshold values. Varying viscosities of the liquids complicate the matter even further.

Even further problems are caused by pressure oscillations that is caused by rapid acceleration or deceleration of the metering needle or tube. This causes the liquid to move within the metering line, which of course causes pressure variations in the line. This oscillation effectively disturbs the pressure signal that is monitored. It would be easy to avoid this problem by lengthening the cycle times of the apparatus so that the oscillation is dampened. This is not possible since a fast operation and output is required of these apparatuses whereby it is not affordable to use unnecessary waiting times. For this reason the signal must be filtered. This requires more complicated programming and may cause loss of data and lead to faulty results. On small metering volumes like 1 or 2 µl the changes in the measured pressure signal are weak and they tend to be covered by disturbances in the measured signal. Most apparatuses cannot control the metering of such a small volumes.

The mechanical condition of the metering line cannot normally be detected by these methods. Therefore it is examined separately by following the washing pressures of the line in order to detect leaks and other possible mechanical faults. It must be noted that leakage of the metering line leads to faulty metering that can be left unnoticed when these methods are used.

The above described methods yield lost of data on the measurement act, but that data is in such a format that it cannot be easily and reliably used for simply detecting the success of a single metering act. The pressure information over the whole metering act is not needed. It would be desirable to have a method wherein a simple indication of a faulty metering is reliably obtained.

SUMMARY OF THE INVENTION

According to the present invention the metering act is performed normally and the liquid to be metered is displaced thereafter in a desired vessel. During the metering act and after a desired amount of liquid is sucked into the metering line, a supplementary suction step is performed wherefrom the success of the metering act can be deduced.

According to another aspect of the present invention, the pressure function of the supplementary suction step is measured and this function is compared with a calibration function.

Other objects and features of the invention will become apparent from the following detailed description considered in conjunction with the accompanying drawings. It is to be understood, however, that the drawings are intended solely for purposes of illustration and not as a definition of the limits of the invention, for which reference should be made to the appended claims.

BENEFITS OF THE INVENTION

The most valuable benefits of the invention are increased reliability of the metering act and simplified processing of the information. No complicated algorithms are needed and the calibration curves or functions are easily obtainable. The control method is independent from the actual metering act and the supplementary suction is done always by same volume. So there are no varying volumes or different metering procedures. Since only one volume is used even one calibration or comparison curve or function is needed. The moment of the test can be chosen so that there is no danger of pressure oscillation in the metering line whereby less signal filtering is needed. This simplifies the process even further. The problematic suction volumes of 1-2 μl do not have to be monitored. The volume of the supplementary suction is at least 3 μl, typically 3-5 μl. This amount is sufficient to yield proper signal in all circumstances.

The calculation algorithms are simple. All meterings having a pressure curve that deviates from the calibration curve are faulty. The reason for failed metering has not to be clarified since all failed meterings have to be discarded. However, if more control terms are used, even the probable cause for failure can be determined. Repeatability of the method is excellent and it is easy to separate successful and failed meterings. One possibility for sorting the meterings is to use a differential curve that is calculated by deducting values of a measures curve from a calibration curve point by point. Herein threshold values can be set for deviations. A deviation greater than one or more threshold values indicates then a failed metering from a successful one.

The metering line is normally filled with distilled water in order to prevent failed metering caused by compressing air during suction of the liquid. The method according to the invention can even detect leaks in the system or possible air that has entrained in the system. Both leaks and air lead to a failed metering.

Figure 1:
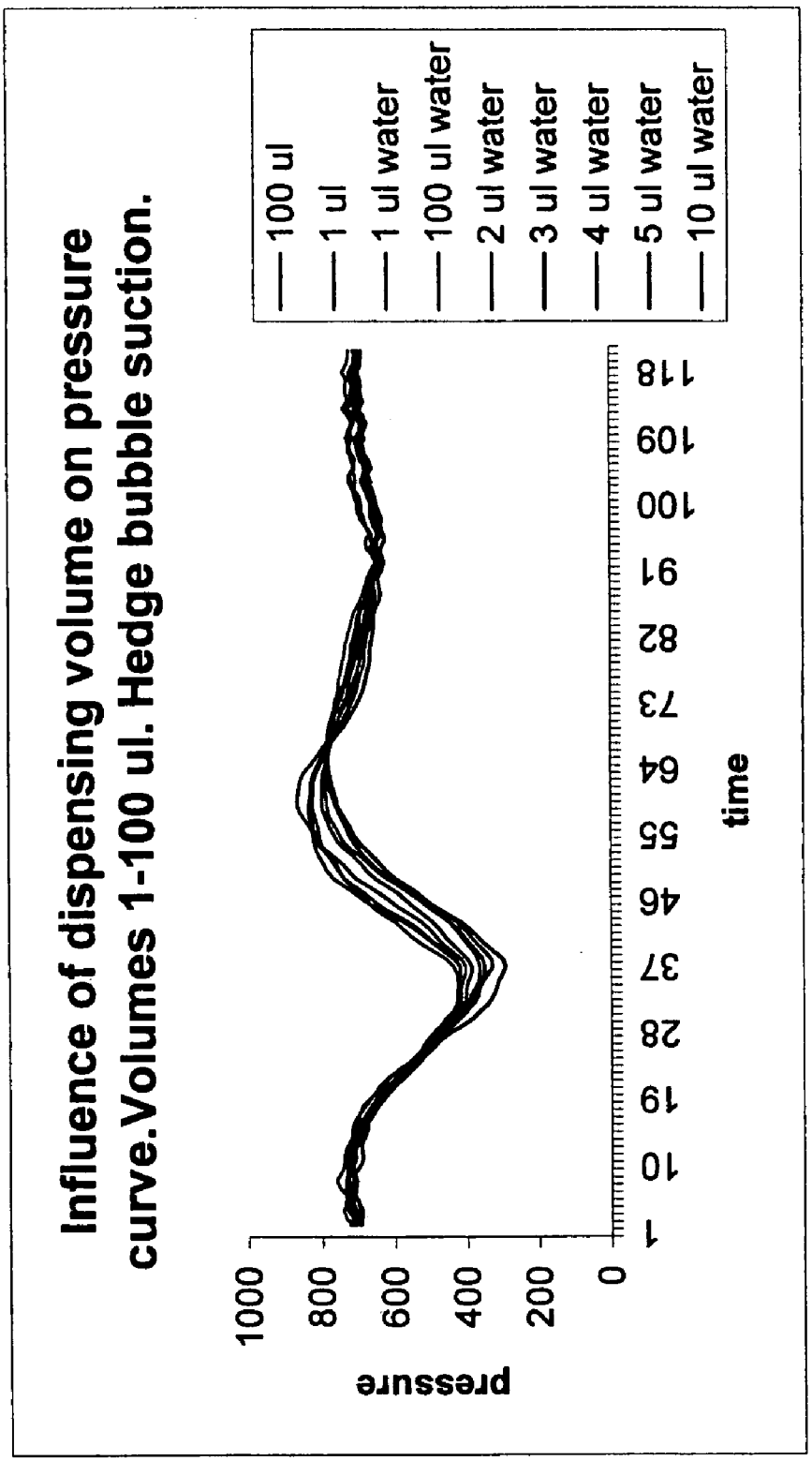
FIG. 1 is a diagram of the effect of volume to the pressure curve.

In the figures only relative values are presented. The scales do not present any actual SI-units.

DETAILED DESCRIPTION OF THE PRESENTLY PREFERRED EMBODIMENTS

A normal dispensing apparatus for metering liquid samples, and reagents in an automatic analyzer comprises a metering line having a hollow needle, a suction tube or similar device for picking the sample from a vessel. The metering line is connected to a metering syringe and a pressure gauge. In order to achieve an accurate measuring result, the metering line is filled with distilled water as described above. Typical metering act starts by inserting the needle into a vessel containing a volume of liquid to be metered. The needle is submerged under the surface of the liquid and suction is effected on the metering line by metering syringe. The length of the movement of the plunger of the syringe determines the volume of the liquid that is sucked in the metering line. Since the line is filled with water, only an amount that is determined by the movement of the plunger can enter the metering line. When a desired amount of liquid has been collected, the needle is moved to another vessel and the volume of liquid is dispensed therein by moving the plunger of the syringe.

Main faults that can occur on dispensing and metering are clogging of the metering line or the desired amount of liquid is sucked in only partially. Since many substances, for example serum or blood, that are handled by analyzers clog easily, it is essential to monitor possible clogging. The substances may also form foam, whereby the level of the liquid is lowered and the surface of the liquid cannot be accurately detected. This leads easily to a partial metering of the desired volume. The vessels may also be empty or only partially full because of human errors or other reasons. Further faults can be caused by leaks in the metering line and air that may be entrained in the metering line.

The invention makes it possible to monitor occurrence of failures in metering very easily. According to the invention, a supplementary suction step is performed after the initial suction step for sucking in the liquid is finished. The pressure in the metering line is measured during the supplementary suction step and pressure curve dependent of time is determined. This pressure curve is compared to a calibration curve. The idea of this supplementary suction and the pressure measurement related thereto is to find out the state of the system after the suction of the volume of liquid. Deviation of a pressure curve from the pressure curve of a normally operating apparatus indicates that something has gone wrong and the metering should be rejected. It is not necessary to determine the actual reason for the failure since the volume of liquid must then be rejected in any case. However, different disturbances cause different kind of deviations in the pressure curve whereby it is possible to detect causes of failures too.

If the reason and cause relation is known it is possible to detect from the state of the system what has actually happened during previous process step, in this case during suction or ejection of the liquid. The supplementary suction indicates whether any liquid has entered, if the liquid volume is same as desired or has the volume entered only partially. Pressure measurement indicates also the viscosity of the liquid and whether the volume includes undesired air bubbles. Clotting is also indicated.

The liquid volume in the supplementary suction step is small, about 3-5 μl and preferably at least 3 μl so that sufficiently strong signal is formed for pressure measurement. The supplementary suction step is performed preferably after the needle is raised from the liquid after the metering suction step.

Figure 4:
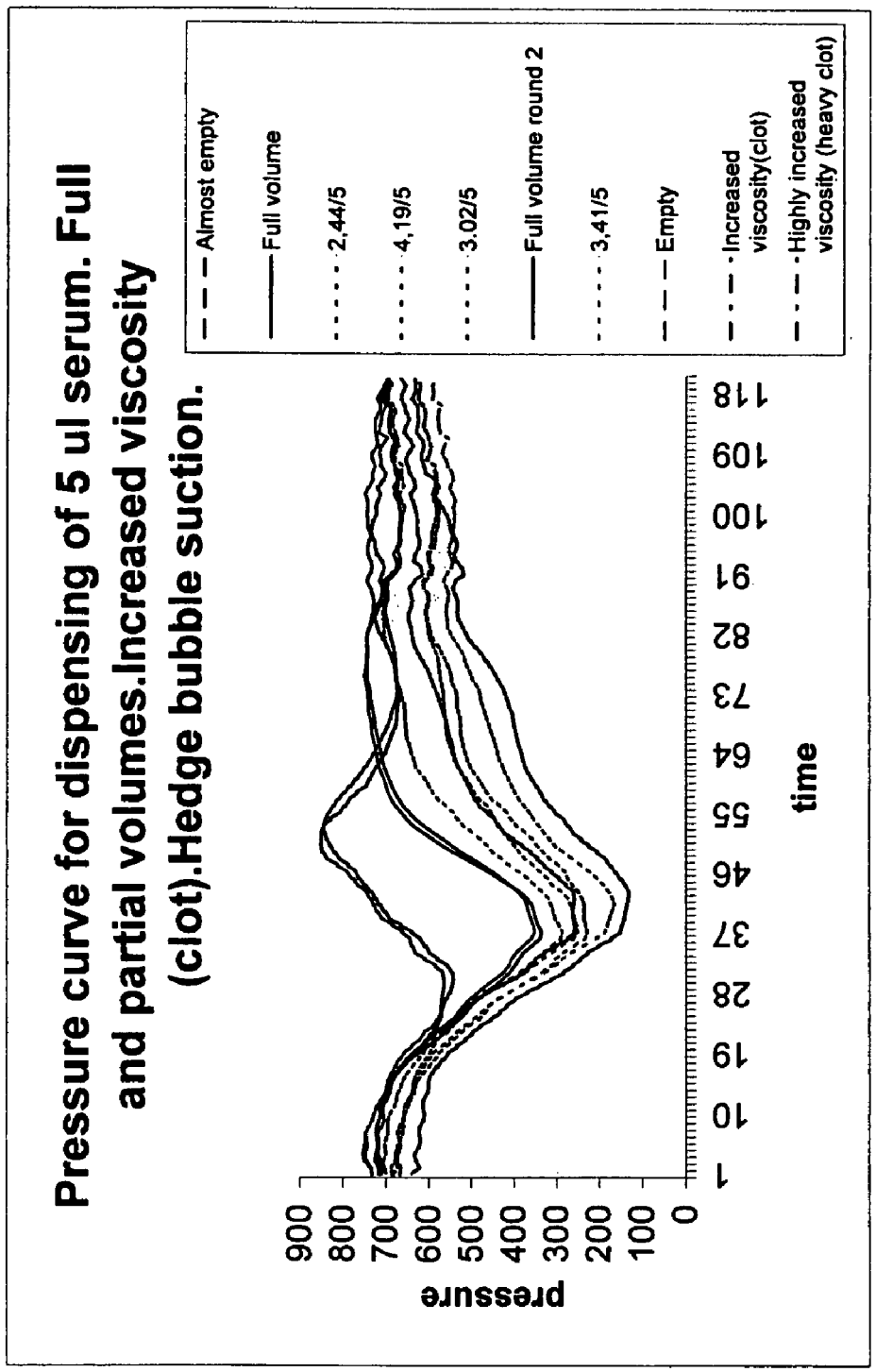
FIG. 4 shows pressure curves two successful meterings and different types of faulty meterings.

In FIG. 4 it is shown different types of pressure curves for successful meterings and different types of faulty meterings. The two curves showing highest pressures are pressure curves for empty and almost empty meterings. It can be seen that when no liquid is sucked into the probe or tip, the pressure in the line is decreased only a little and after the initial suction the pressure rises higher than at the beginning. Since the liquid in this case does not provide any, or provides only a little, resistance for sucking action, the pressure is not lowered. Two curves below the above mentioned show successful measurements. The curves below successful meterings show incomplete meterings and two meterings including increased viscosity (a clot). It can be seen that both incomplete metering caused by suction of only a partial amount of liquid and increased viscosity cause a drop in the pressure curve. It can also be seen that on partial meterings and for clots the pressure rises more slowly to the initial pressure. The heavy clot is the lowest curve in the diagram. If desired, the pressure curves can be analyzed mathematically and the types of the possible faults can be detected from the shape and position of the curves.

Figure 2:
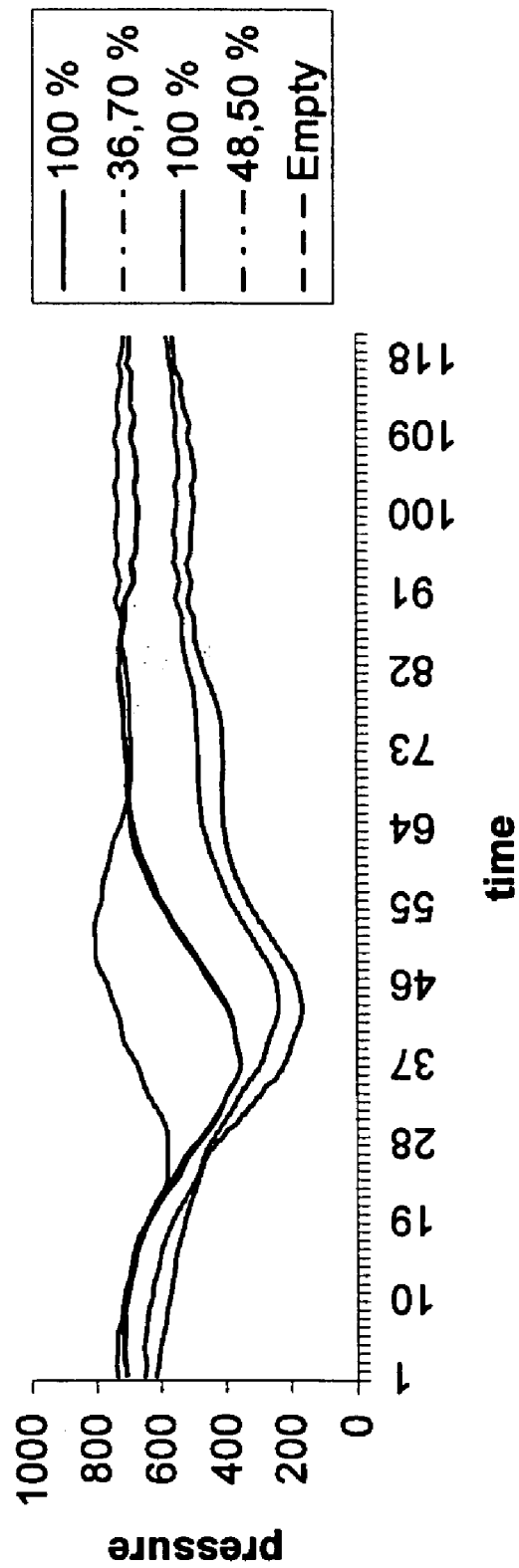
FIG. 2 shows the effect of partial metering on the pressure curve.
Figure 3:
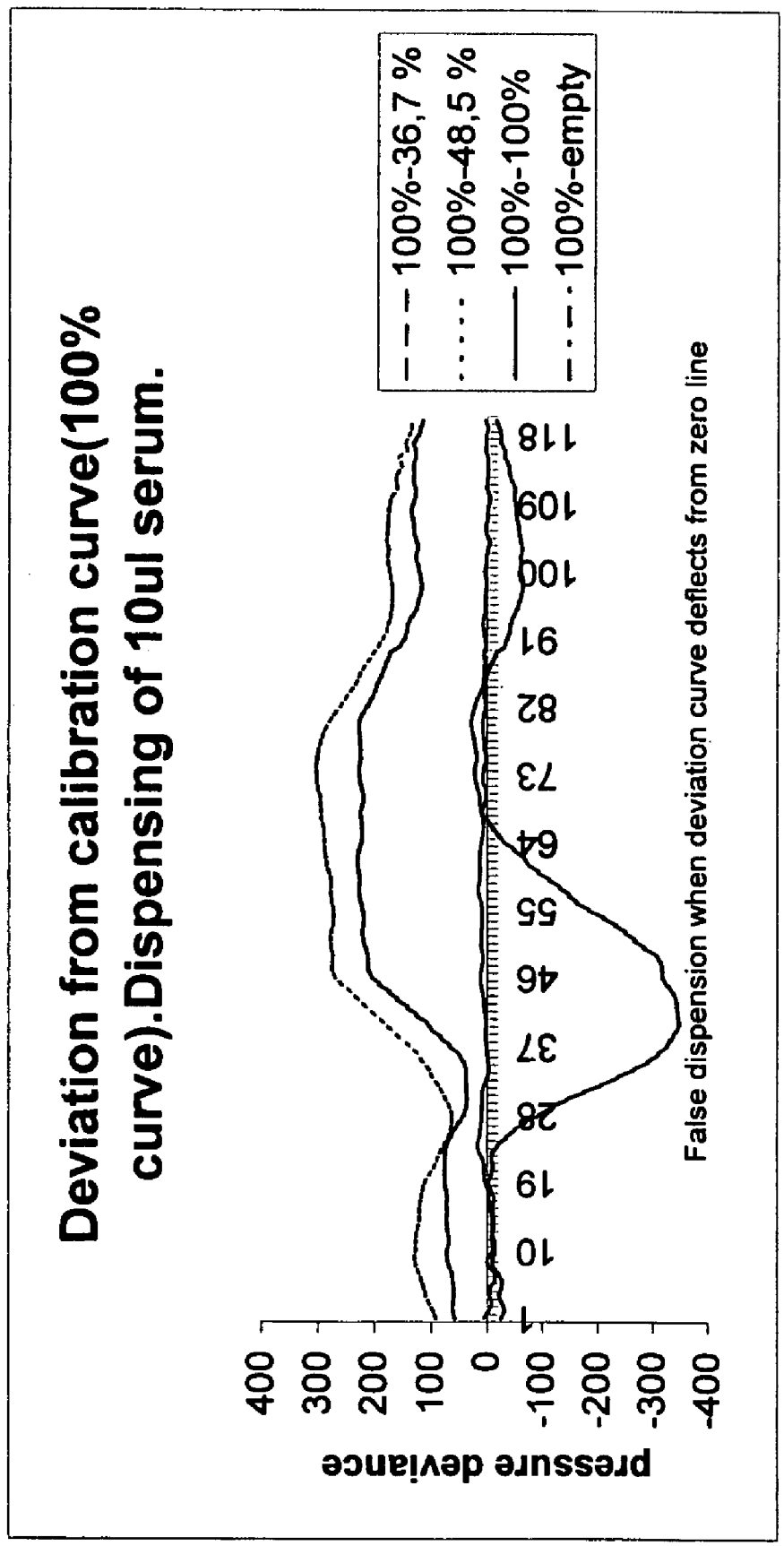
FIG. 3 shows deviations from the calibration curve of pressure curves of FIG. 2.

FIG. 1 shows the effect of the dispensing or metering volume on the pressure curve of the supplementary suction. It can be clearly seen that the metered volume of the liquid does not essentially affect the pressure curve. Therefore in principle only one calibration curve is heeded for one substance regardless of the volume to be metered and dispensed. FIG. 2 shows pressure curves of dispensing 10 μl serum. It can be seen, that smaller the actually entered volume, lower the pressure drop. It must be noticed that the system is not supposed to detect the actual volume that is entered into the metering line but simply indicate that desired amount of liquid could not be sucked. The pressure difference herein is caused by partial filling of the space in the metering line, not by the actual volume of the liquid sample itself. The FIG. 3 illustrates how the deviation from the calibration curve can be used for rejecting faulty meterings. This can be done e.g. by simply subtracting the values of the actual measured pressure curve from the calibration curve. The deviation from the zero line indicates false dispension. Of course, suitable threshold values must be used so that no unnecessarily large amounts of rejections are obtained.

The calibration curve can be obtained by normal calibration methods by using the supplementary suction step and measuring the curve obtained. The properties of the liquid handled and the faultless operation of the apparatus must naturally be ensured during calibration. Each substance showing a high difference in viscosity requires a different calibration curve.

Instead of comparing to a calibration curve, the invention can be implemented so that all measured pressure curves for a certain amount of measured liquid volumes are recorded and they are then compared to each other and samples having non-compliant pressure curve are discarded. This method is anyhow comparatively slow in calibration procedure and probably less user-friendly than the above described method. Very rough control can be accomplished by simply using a general comparison curve that has approximately same shape as an actual pressure curve. The shapes of the curves can be compared and samples having curves of different shape can be discarded.

If it is known, for example from previous calibration measurements, how the change of volume changes the calibration curve, only a single calibration curve can be used for several volumes. Herein the actual calibration curve that is used is calculated on basis of the basic calibration curve for a known volume.

The supplementary suction can be used for checking the completeness of the ejection of the volume of liquid. Then the calibration curve is the pressure curve for a dispensing with no sample. The ejection of the liquid is anyhow so reliable that this control is seldom needed.

Thus, while there have been shown and described and pointed out fundamental novel features of the invention as applied to a preferred embodiment thereof, it will be understood that various omissions and substitutions and changes in the form and details of the method may be made by those skilled in the art without departing from the spirit of the invention. For example, it is expressly intended that all combinations of these elements and/or method steps which perform substantially the same results are within the scope of the invention. Substitutions of the elements from one described embodiment to another are also fully intended and contemplated. It is also to be understood that the drawings are not necessarily drawn to scale but they are merely conceptual in nature. It is the intention, therefore, to be limited only as indicated by the scope of the claims appended hereto.

What is claimed is:

1. Method for controlling the dispensation of a liquid volume sample when metering amounts of liquid by sucking into a tube, dispensing probe or disposal tip a volume of a liquid to be displaced and later ejecting the sample to a different vessel, comprising steps of
sucking a volume of liquid into a tube,
performing a supplementary sucking step,
measuring the pressure during the supplementary sucking step,
obtaining a pressure/time curve on basis of the pressure measurement, and
determining on basis of the pressure curve whether the suction of the volume of liquid has been performed successfully.

2. Method according to the claim 1, wherein determining whether the suction of the volume of liquid has been performed successfully is performed by comparing the pressure curve to a calibration pressure curve.

3. Method according to the claim 1, wherein determining whether the suction of the volume of liquid has been performed successfully is performed by comparing the pressure curve to a calibration pressure curve by e.g. subtracting the values of the actual measured pressure curve from one or several calibration curves and checking if any set threshold values are exceeded.

4. Method according to claim 1, wherein the volume of the supplementary suction is at least 3 µl, preferably 3-5 µl.

5. Method according to claim 1, wherein the supplementary suction is performed after the tube is raised off from the liquid that is sucked.

6. Method according to claim 2, wherein the same calibration curve is used for several volumes of one type of liquid.

7. Method according to claim 1, wherein one calibration curve for a single volume is used as basis of measurements for several volumes of one type of liquid and a calibration curve for each volume to be dispensed is calculated on basis of the one calibration curve.

8. Method according to claim 2, wherein the volume of the supplementary suction is at least 3 µl, preferably 3-5 µl.

9. Method according to claim 3, wherein the volume of the supplementary suction is at least 3 µl, preferably 3-5 µl.

10. Method according to claim 2, wherein the supplementary suction is performed after the tube is raised off from the liquid that is sucked.

11. Method according to claim 3, wherein the supplementary suction is performed after the tube is raised off from the liquid that is sucked.

12. Method according to claim 4, wherein the supplementary suction is performed after the tube is raised off from the liquid that is sucked.

13. Method according to claim 3, wherein the same calibration curve is used for several volumes of one type of liquid.

14. Method according to claim 4, wherein the same calibration curve is used for several volumes of one type of liquid.

15. Method according to claim 5, wherein the same calibration curve is used for several volumes of one type of liquid.

16. Method according to claim 2, wherein one calibration curve for a single volume is used as basis of measurements for several volumes of one type of liquid and a calibration curve for each volume to be dispensed is calculated on basis of the one calibration curve.

17. Method according to claim 3, wherein one calibration curve for a single volume is used as basis of measurements for several volumes of one type of liquid and a calibration curve for each volume to be dispensed is calculated on basis of the one calibration curve.

18. Method according to claim 4, wherein one calibration curve for a single volume is used as basis of measurements for several volumes of one type of liquid and a calibration curve for each volume to be dispensed is calculated on basis of the one calibration curve.

19. Method according to claim 5, wherein one calibration curve for a single volume is used as basis of measurements for several volumes of one type of liquid and a calibration curve for each volume to be dispensed is calculated on basis of the one calibration curve.

20. Method according to claim 6, wherein one calibration curve for a single volume is used as basis of measurements for several volumes of one type of liquid and a calibration curve for each volume to be dispensed is calculated on basis of the one calibration curve.

* * * * *